United States Patent
Woudenberg et al.

(10) Patent No.: US 9,351,473 B2
(45) Date of Patent: May 31, 2016

(54) HIGH TEMPERATURE GERMINATING LETTUCE SEEDS

(71) Applicant: RIJK ZWAAN ZAADTEELT EN ZAADHANDEL B.V., De Lier (NL)

(72) Inventors: Leendert Jacobus Woudenberg, Vlaardingen (NL); Gerardus Maria Lenssen, Delfgauw (NL); Johannes Wilhelmus Schut, Wouw (NL); Eric Roland Coppoolse, Poortugaal (NL)

(73) Assignee: RIJK ZWAAN ZAADTEELT EN ZAADHANDEL B.V., De Lier (NL)

( * ) Notice: Subject to any disclaimer, the term of this patent is extended or adjusted under 35 U.S.C. 154(b) by 253 days.

(21) Appl. No.: 13/836,277

(22) Filed: Mar. 15, 2013

(65) Prior Publication Data

US 2014/0283223 A1    Sep. 18, 2014

(51) Int. Cl.
*A01H 5/12*    (2006.01)

(52) U.S. Cl.
CPC .................................... *A01H 5/12* (2013.01)

(58) Field of Classification Search
None
See application file for complete search history.

(56) References Cited

PUBLICATIONS

Argyris et al, Apr. 11, 2010, Theor Appl Genet, vol. 122, pp. 95-108.*

Andres R. Schwember, et al. "A genetic locus and gene expression patterns associated with the priming effect on lettuce seed germination at elevated temperatures" Plant Mol Biol 73:105-118, Jan. 2010.
Tingting Dong, et al. "Nitrate, abscisic acid and gibberellin interactions on the thermoinhibition of lettuce seed germination" Plant Growth Regul 66:191-202, 2012.
Jason Argyris, et al. "Genetic Variation for Lettuce Seed Thermoinhibition is Associated with Temperature-Sensitive Expression of Abscisic Acid, Gibberellin, and Ethylene Biosynthesis, Metabolism, and Response Genes" Plant Physiology 148:926-947, Oct. 2008.

* cited by examiner

*Primary Examiner* — Eileen B O Hara
(74) *Attorney, Agent, or Firm* — Vedder Price P.C.; Thomas J. Kowalski; Deborah L. Lu

(57) ABSTRACT

The present invention relates to lettuce plants (*Lactuca sativa* L.) which may comprise a genetic determinant, which when homozygous present in a seed, provides the seed in an unprimed state with the capability to germinate at a high temperature, which genetic determinant is obtainable from a lettuce plant which may comprise said genetic determinant, representative seed which was deposited with the NCIMB under accession number NCIMB 41914, NCIMB 41915, NCIMB 41916, NCIMB 41917, NCIMB 41918, NCIMB 41919, NCIMB 41922, NCIMB 41923, and NCIMB 41926.

16 Claims, 2 Drawing Sheets

HIGH TEMPERATURE GERMINATING LETTUCE SEEDS

INCORPORATION BY REFERENCE

All documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

The present invention relates to seed of lettuce (*Lactuca sativa* L.) plants, capable of germinating at a high temperature. The invention further relates to parts of the plants, in particular the seeds, to other propagation material, and to progeny of the plants.

BACKGROUND OF THE INVENTION

Lettuce (*Lactuca sativa* L.) originates from Mediterranean regions where the summers are long, hot, and dry. Lettuce seedlings have the highest survival prospects when emerging from seeds in early spring. To avoid premature germination during summer, lettuce seeds are equipped with a secondary (or induced) dormancy mechanism called thermo-inhibition. During the heat of summer, thermo-inhibition prevents seeds from germinating during a short period of auspicious circumstances, such as a single rain-shower. Only during the relative long cold of winter, thermo-inhibition is relieved, thus enabling germination to occur when temperatures rise in early spring.

During the domestication of lettuce, thermo-inhibition was maintained. Most commercial lettuce seeds are inhibited from germinating at high temperatures, the exact temperature is dependent on the cultivar and the seed production environment. This means that modern lettuce cultivars, when sown in hot conditions, will go into dormancy. This is especially problematic for winter lettuce growing areas, where permissive germination temperatures are exceeded during the late summer and autumn planting season.

The optimal germination temperature for the majority of lettuce varieties lies between 15° C. to 22° C. To obtain lettuce seeds capable of germinating at temperatures well above 22° C., seeds are subjected to a rather expensive germination stimulating process called "priming". Seed priming allows for the controlled hydration of seeds, allowing the seeds to complete the first steps in the germination process before they are dried back to their original moisture content, and stored until planting. One of the primary benefits of seed priming is the ability to alleviate thermo-inhibition by increasing the maximum temperature at which germination will occur.

Although seed priming may be beneficial to seed germination, it is an expensive procedure in terms of labour and equipment requirements, the types of ingredients that are used, and the time it requires for hydrating and drying back the seeds. In addition, the priming process may result in a reduction of the shelf life of primed seeds, as compared to untreated seeds. This undesirable side effect is influenced by the rate and extent of the drying back procedure.

Moreover, there is an inherent risk of "overpriming" which may lead to damage of the radical tips of the seeds, and subsequently, poor seedling growth. Overpriming would render primed seeds useless, thus making elaborate seed quality checks an additional necessity of the priming process.

By developing seeds of the species *Lactuca sativa* L. that are capable of germinating at high temperatures without the need for priming, the expensive and potentially precarious process of seed priming becomes obsolete.

Improving the capability of lettuce seeds to germinate at a high temperature may also enlarge the total acreage for lettuce cultivation. Areas of the world with relatively warm winters are unsuitable for lettuce cultivation, since the germination capabilities of current lettuce varieties are insufficient to overcome thermo-inhibition under such high temperatures.

In a more global context, rising temperatures due to global warming may have a considerable impact on soil temperature. As such, high temperature, and the resulting increase in soil temperatures, is considered a significant environmental stress that may limit worldwide crop productivity in the near future.

Citation or identification of any document in this application is not an admission that such document is available as prior art to the present invention.

SUMMARY OF THE INVENTION

It is the object of the present invention to provide lettuce seeds with an improved capability to germinate at a high temperature. In turn, this would reduce or eliminate the need for costly priming treatments, and potentially increase the total acreage for lettuce cultivation.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

DEPOSIT INFORMATION

Seeds of *Lactuca sativa* plants exhibiting improved germination capability at high temperatures were deposited under NCIMB deposit accession numbers 41914, 41915, 41916, 41917, 41918, 41919, 41922, 41923, and 41926 on 4 Jan. 2012 with NCIMB Ltd. (Ferguson Building, Craibstone Estate, Bucksburn, Aberdeen, AB21 9YA). All seeds of the deposit comprise the genetic determinant homozygously.

It should be noted that the deposited seeds are the result of a mutagenesis treatment and do not meet the DUS criteria which are required for obtaining plant variety protection, and may therefore not be considered to be plant varieties.

The Deposits with NCIMB Ltd, Ferguson Building, Craibstone Estate, Bucksburn, Aberdeen AB21 9YA, UK, under deposit accession numbers deposit accession numbers 41914, 41915, 41916, 41917, 41918, 41919, 41922, 41923, and 41926 were made pursuant to the terms of the Budapest Treaty. Upon issuance of a patent, all restrictions upon the deposit will be removed, and the deposit is intended to meet the requirements of 37 CFR §§1.801-1.809. The deposit will be maintained in the depository for a period of 30 years, or 5 years after the last request, or for the effective life of the patent, whichever is longer, and will be replaced if necessary during that period.

BRIEF DESCRIPTION OF THE DRAWINGS

The following detailed description, given by way of example, but not intended to limit the invention solely to the specific embodiments described, may best be understood in conjunction with the accompanying drawings.

DETAILED DESCRIPTION OF THE INVENTION

Figure 1A:
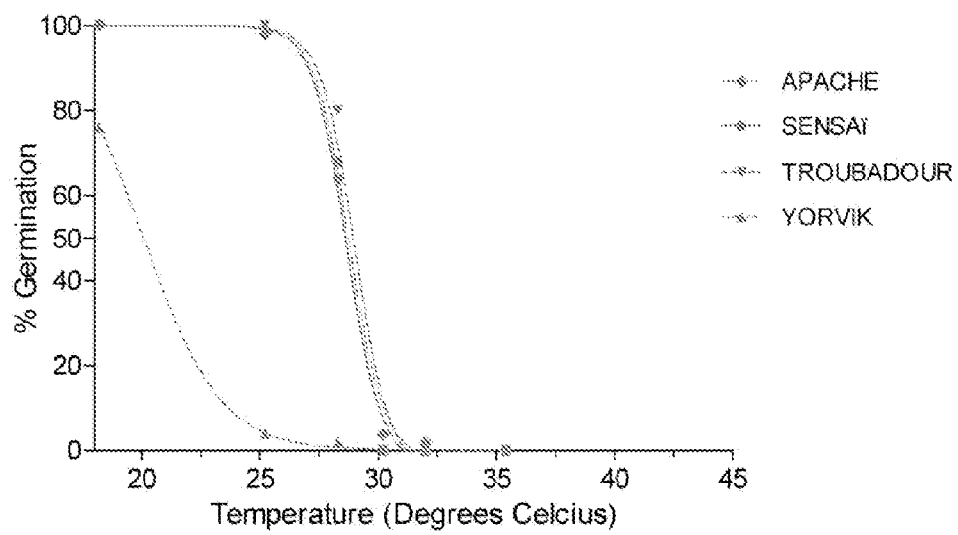
FIG. 1A: Graph showing the final germination percentages over a given temperature range, for wild type seed lots of Apache, Sensaï, Troubadour, and Yorvik. The GT50 Dark is the temperature at which the final germination percentage is expected to be 50%.

In the research leading to the present invention, new seeds of the species *Lactuca sativa* L. were developed which have the surprising capability to germinate at a high temperature, without the need for priming.

The said capability to germinate at a high temperature is controlled by a genetic determinant, the inheritance which is consistent with that of a monogenic recessive trait. The term "recessive trait" is to mean in the context of this application that the fully achievable trait is only observable in seeds of a lettuce plant which may comprise the genetic determinant in the homozygous state. Since the inheritance of the trait is comparable to that of a monogenic trait, it is advantageous in that the trait may easily be incorporated into various cultivated lettuce types.

The present invention thus provides seeds of the species *Lactuca sativa* L., which in an unprimed state exhibits the capability to germinate at a high temperature as a result of the genetic determinant which is as found in seeds of which a representative sample was deposited under NCIMB deposit accession numbers NCIMB 41914, NCIMB 41915, NCIMB 41916, NCIMB 41917, NCIMB 41918, NCIMB 41919, NCIMB 41922, NCIMB 41923, and NCIMB 41926.

Therefore, the invention also relates to plants of the species *Lactuca sativa* L. which may comprise said genetic determinant, which when homozygously present in a seed, provides the seed in an unprimed state with the capability to germinate at a high temperature.

Lettuce seed germination is strongly temperature dependent. If the temperature increases above the optimum germination temperature, the germination percentage declines sharply. Thus the germination temperature of a seed lot may be measured in terms of the "Germination Temperature 50" (GT50), which is the temperature at which there is a 50% reduction in germination. When seeds of a given seed lot are exposed to temperatures above the GT50, they may become thermodormant or die. The GT50 may differ amongst different cultivars.

"Seed lot" as used in this application is to mean, a batch of seeds produced from a mother plant. A seed lot consists preferably of a minimum of 100 seeds. When less than 100 seeds are used to determine the GT50 of a seed lot, the GT50 becomes less accurate.

The upper temperature cut-off point "GT50 Dark", as used in this application is to mean, the temperature at which 50% of the seeds having the genetic determinant will germinate when sown on paper in the dark. The GT50 Dark is measured under continuous dark conditions (24 h/day) as this mimics germination conditions when seeds are planted beneath the soil or when seeds are encapsulated in pellets. Exposure of seeds belonging to the seed lot above the GT50 Dark, may cause the seeds to become thermodormant or die.

The skilled person is able to determine the GT50 Dark of a seed lot using a two step method. Firstly, germination tests are performed at different temperatures, preferably between 18° C. to 42° C., in order to determine the cumulative germination percentage over time at a given temperature. For each seed lot to be tested, preferably 100 seeds are sown on top of a round filter paper wetted with tap water. These are in turn placed inside of a non-transparent plastic tray, which itself is lined with a large square piece of beet filter paper also wetted with tap water. A temperature recording device is placed on the beet filter paper to record the actual germination temperature at seed level. The tray is then closed with a well-fitted non-transparent lid, and placed inside a dark plastic bag. The tray is then placed inside a pre-heated incubator at the desired temperature. Biological replicates are preferably sown in different trays and at different points of time to remove any biases related to sowing.

All precautions should be taken to ensure that the germination tests are performed under dark conditions. Setting up tests, the incubations and germination scoring is performed preferably inside a thermostable room, which is closed from all outside light sources. Additionally, the thermostable room is lit with for example, green safe lights (Philips TL-D 36W/17 Green) to prevent any light effects on germination.

Germination is preferably scored twice a day. As used herein, "germination" occurs for example, when radical protrusion is visible. "Germination over Time" curves may then be plotted in order to show the cumulative germination percentage of a seed lot over time, at a set temperature. The final germination percentage for a given seed lot at a given temperature may be derived from the "Germination over Time" curves. As used herein, the "final germination percentage" is the percentage of germination of a seed lot, after which no more germination occurs.

Figure 1B:
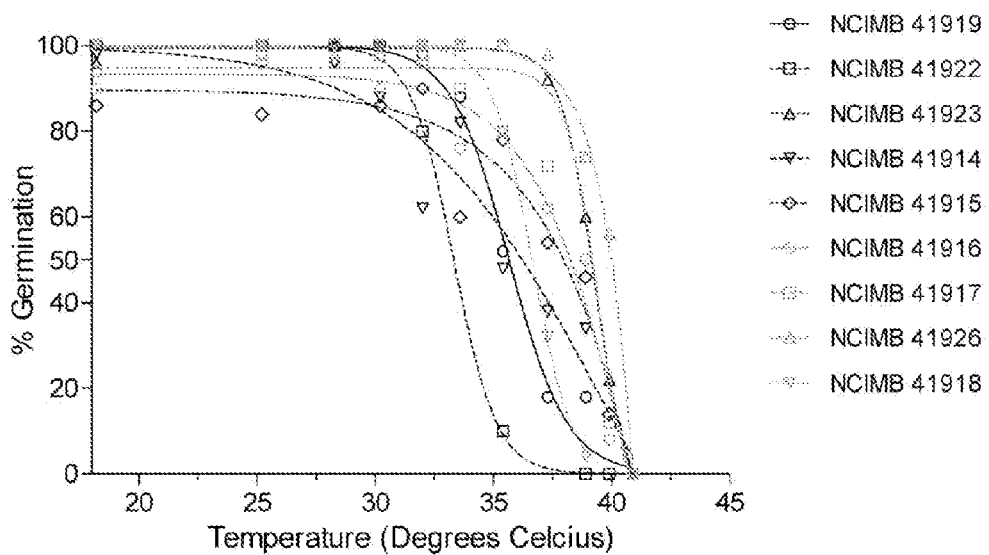
FIG. 1B: Graph showing the final germination percentages over a given temperature range, for mutant seed lots. The GT50 Dark is the temperature at which the final germination percentage is expected to be 50%.
Figure 1C:
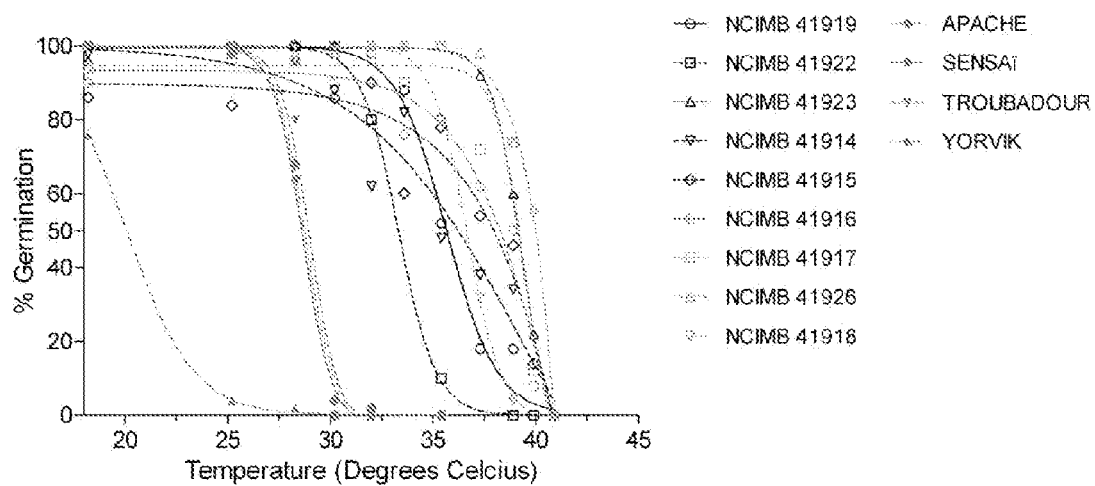
FIG. 1C: Graph showing the final germination percentages over a given temperature range, for both wild type and mutant seed lots together. The GT50 Dark is the temperature at which the final germination percentage is expected to be 50%.

The final germination percentage from each "Germination over Time" curve is then plotted per actual measured temperature, from 18° C. to 42° C. (FIGS. 1A, 1B and 1C). A line of best fit is used for example, to fit the final germination percentages into a curve for each seed lot. The skilled person is familiar with this practice.

From the line of best fit, the GT50 Dark may be determined per seed lot. The GT50 Dark corresponds to the temperature at which the final germination percentage is expected to be 50%. When seeds of a given seed lot are exposed to temperatures above the GT50 Dark, they may become thermodormant or die.

In one embodiment, the invention relates to a seed lot of the species *Lactuca sativa* L. wherein the seeds belonging to the seed lot comprise a genetic determinant, which when homozygously present, provides the seeds in an unprimed state with the capability to germinate at a high temperature, and which seed lot is characterized in that the GT50 Dark of said seed lot is at least 6.2° C. higher than the GT50 Dark of a seed lot of seeds not which may comprise the genetic determinant, and wherein said genetic determinant is as present in or obtainable from seeds of which a representative sample has been deposited under accession number NCIMB 41914, NCIMB 41915, NCIMB 41916, NCIMB 41917, NCIMB 41918, NCIMB 41919, NCIMB 41922, NCIMB 41923, and NCIMB 41926.

In one embodiment, the invention relates to a seed lot of the species *Lactuca sativa* L. wherein the seeds belonging to the seed lot comprise a mutation, which when homozygously present, provides the seeds in an unprimed state with the capability to germinate at a high temperature, and which seed lot is characterized in that the GT50 Dark of said seed lot is at least 6.2° C. higher than the GT50 Dark of a seed lot of seeds not which may comprise the mutation, and wherein said mutation is as present in or obtainable from seeds of which a representative sample has been deposited under accession number NCIMB 41914, NCIMB 41915, NCIMB 41916, NCIMB 41917, NCIMB 41918, NCIMB 41919, NCIMB 41922, NCIMB 41923, and NCIMB 41926.

In the context of this application the genetic determinant of the invention may mean a gene, a locus, an allele or a mutation therein. The genetic determinant is the underlying genetic element that causes the phenotypic trait of the invention. The "phenotypic trait" is the phenotype in which a seed in an unprimed state has the capability to germinate at a high temperature in the dark. "Genetic trait", "trait", "trait of the invention", and "phenotypic trait" may be used interchangeably.

In another embodiment, the invention relates to a seed lot of the species *Lactuca sativa* L. wherein the seeds belonging to the seed lot comprise a genetic determinant, which when homozygously present, provides the seeds in an unprimed state with the capability to germinate at a high temperature, and further characterized in that the GT50 Dark of said seed lot is at least 31.8° C.

In another embodiment, the invention relates to a lettuce seed belonging to a seed lot, wherein the seed may comprise the genetic determinant, which when homozygously present, provides the seed in an unprimed state with the capability to germinate at a high temperature, and which is characterized in that the GT50 Dark of said seed lot is at least 6.2° C. higher as compared to a seed belonging to a seed lot not comprising the genetic determinant, and wherein said genetic determinant is as present in or obtainable from the seeds of which a representative sample has been deposited under accession number NCIMB 41914, NCIMB 41915, NCIMB 41916, NCIMB 41917, NCIMB 41918, NCIMB 41919, NCIMB 41922, NCIMB 41923, and NCIMB 41926.

The said seed may comprise a genetic determinant, which when homozygously present, provides the seeds in an unprimed state with the capability to germinate at a high temperature, in particular at a temperature of at least 31.8° C.

The GT50 Dark of said seed lot or the germination temperature of the seed is preferably, in order of increased preference, between 6.5° C. and 22° C., between 7° C. and 22° C., between 8° C. and 22° C., between 9° C. and 22° C., between 10° C. and 22° C., between 11° C. and 22° C., between 12° C. and 22° C., between 13° C. and 22° C., between 14° C. and 22° C., between 15° C. and 22° C., between 16° C. and 22° C. between 17° C. and 22° C. between 18° C. and 22° C. between 19° C. and 22° C. between 20° C. and 22° C. and between 21° C. and 22° C. higher.

The GT50 Dark of the seed lot or the germination temperature of the seed lies preferably, in order of increased preference, between 31.8° C. and 42° C., between 32° C. and 42° C., between 33° C. and 42° C., between 34° C. and 42° C., between 35° C. and 42° C., between 36° C. and 42° C., between 37° C. and 42° C., between 38° C. and 42° C., between 39° C. and 42° C., between 40° C. and 42° C., between 41° C. and 42° C.

In one embodiment, the invention relates to a lettuce plant of the species *Lactuca sativa* L. carrying a genetic determinant, which when homozygously present in a seed, provides the seed in an unprimed state with the capability to germinate at a high temperature. The high temperature is as defined above.

In another embodiment, the invention relates to a lettuce plant of the species *Lactuca sativa* L. carrying a genetic determinant, which when homozygously present in a seed, provides the seed in an unprimed state with the capability to germinate at a high temperature, and wherein said genetic determinant is as present in the genome of plants grown from seeds of which a representative sample was deposited under accession number NCIMB 41914, NCIMB 41915, NCIMB 41916, NCIMB 41917, NCIMB 41918, NCIMB 41919, NCIMB 41922, NCIMB 41923, and NCIMB 41926.

Accordingly, a lettuce plant of the invention is a plant that is grown from *Lactuca sativa* L. seed carrying the trait of the invention, or a *Lactuca sativa* L. plant that produces seeds carrying the trait of the invention.

In one embodiment, the invention relates to a lettuce plant of the species *Lactuca sativa* L. carrying a genetic determinant, which when homozygously present in a seed, provides the seed in an unprimed state with the capability to germinate at a high temperature, and wherein said genetic determinant is obtainable by introgression from a plant grown from seed of which a representative sample was deposited under accession number NCIMB 41914, NCIMB 41915, NCIMB 41916, NCIMB 41917, NCIMB 41918, NCIMB 41919, NCIMB 41922, NCIMB 41923, and NCIMB 41926.

In one embodiment, the invention relates to a lettuce plant of the species *Lactuca sativa* L. carrying a genetic determinant, which when homozygously present in a seed, provides the seed in an unprimed state with the capability to germinate at a high temperature, and wherein said genetic determinant is introgressed from a plant grown from seed that was deposited under accession number NCIMB 41914, NCIMB 41915, NCIMB 41916, NCIMB 41917, NCIMB 41918, NCIMB 41919, NCIMB 41922, NCIMB 41923, and NCIMB 41926.

"Introgression" as used in this application is intended to mean the introduction of a trait into a plant not carrying the trait by means of crossing and selection.

The lettuce plant into which the trait of the invention may be introduced may be for example, a lettuce plant from any one of the types of cultivated lettuce from the following group: iceberg, butterhead, romaine or cos, green leaf, red leaf, lollo, oakleaf, curly, incised leaf, multileaf, cutting, stem, Batavia, and Latin lettuce.

It should be noted that the skilled person will be able to identify any descendants that carry the trait in a further generation, if the selection criteria or criterion is clearly defined. Plants that carry the genetic determinant may suitably be identified amongst descendants from a cross between a plant not carrying the genetic determinant or mutation, and a plant that carries the genetic determinant or mutation in the homozygous state and of which representative seed was deposited under accession number NCIMB 41914, NCIMB 41915, NCIMB 41916, NCIMB 41917, NCIMB 41918, NCIMB 41919, NCIMB 41922, NCIMB 41923, and NCIMB 41926, by growing F2 plants from seeds that are the result of the initial cross and a selfing step, allowing the F2 plants to self and produce F3 seeds and performing germination tests on the F3 seed lots to determine if the GT50 Dark of said seed lot is at least 31.8° C. If the GT50 Dark of the F3 seed lot falls within the said defined range, F2 plants carrying the genetic determinant and showing the desired trait may be selected.

Alternatively, selection may be achieved through identification of the genetic determinant, for example, by means of one or more molecular markers. Markers may be developed accordingly by a skilled person based on the material that was deposited under accession number NCIMB 41914, NCIMB 41915, NCIMB 41916, NCIMB 41917, NCIMB 41918, NCIMB 41919, NCIMB 41922, NCIMB 41923, and NCIMB 41926.

In the absence of molecular markers, or in the event that recombination has occurred between the molecular markers and the genetic determinant and these are not predicative any longer, equivalence of genetic determinants may still be determined by an allelism test. To perform an allelism test, material that is homozygous for the known determinant, a tester plant is crossed with material that is homozygous for the genetic determinant to be tested. This latter plant is referred to as the donor plant. The donor plant to be tested should be or should be made homozygous for the genetic determinant to be tested. The skilled person knows how to obtain a plant that is homozygous for the genetic determinant to be tested. When the GT50 Dark of all F3 seed lots arising from the F2 of the cross between a donor plant and a tester plant have a GT50 Dark of at least 31.8° C., then the phenotype related to the genetic determinant or mutation is observed, and the genetic determinant or mutation of the donor plant and the tester plant have been proven to be equivalent or the same.

In the event that more than one gene is responsible for a certain trait, and an allelism test is done to determine equivalence, the skilled person doing the test has to make sure that all relevant genes are present homozygously in order for the test to work properly.

The invention further relates to progeny of a lettuce plant which may comprise the genetic determinant, which when homozygously present in a seed, provides the seed in an unprimed state with the capability to germinate at a high temperature. Such progeny may be produced by sexual or vegetative reproduction of a plant of the invention or a progeny plant thereof. The progeny carries the genetic determinant that causes the trait of the invention and that is as found in seeds deposited under accession number NCIMB 41914, NCIMB 41915, NCIMB 41916, NCIMB 41917, NCIMB 41918, NCIMB 41919, NCIMB 41922, NCIMB 41923, and NCIMB 41926, in homozygous form.

When the genetic determinant of the invention is homozygously present in an unprimed seed of the progeny plant, the seed has the capability to germinate at a high temperature in the same or in a similar way to an unprimed seed of the plant of which representative seed was deposited under accession number NCIMB 41914, NCIMB 41915, NCIMB 41916, NCIMB 41917, NCIMB 41918, NCIMB 41919, NCIMB 41922, NCIMB 41923, and NCIMB 41926. This means that such progeny has the same characteristics as claimed for lettuce plants of the invention. Additionally, the plant may be modified in one or more other characteristics. Such additional modifications are for example, effected by mutagenesis or by transformation with a transgene.

As used herein, the word "progeny" is intended to mean the offspring or the first and all further descendants from a cross with a plant of the invention that shows the trait of the invention and/or carries the genetic determinant underlying the trait. Such progeny is for example obtainable by crossing a first lettuce plant with a second lettuce plant, wherein one of the lettuce plants was grown from seeds of which a representative sample was deposited under NCIMB accession number NCIMB 41914, NCIMB 41915, NCIMB 41916, NCIMB 41917, NCIMB 41918, NCIMB 41919, NCIMB 41922, NCIMB 41923, and NCIMB 41926, but it may also be the progeny of any other lettuce plant carrying the genetic determinant as present in seeds of deposit NCIMB 41914, NCIMB 41915, NCIMB 41916, NCIMB 41917, NCIMB 41918, NCIMB 41919, NCIMB 41922, NCIMB 41923, and NCIMB 41926.

It is understood that a parent plant that provides the genetic determinant of the invention is not necessarily a plant grown directly from the deposited seeds. The parent may also be a progeny plant from the seed, or a progeny plant from seeds that are identified to have (or to have acquired) the trait of the invention by other means.

In one embodiment, the invention relates to lettuce plants that carry the trait of the invention and that have acquired the said trait by introduction of the genetic information that is responsible for the trait from a suitable source, either by conventional breeding, or genetic modification, in particular by cis-genesis or trans-genesis. Cis-genesis is genetic modification of plants with a natural gene, encoding an (agricultural) trait from the crop plant itself or from a sexually compatible donor plant. Trans-genesis is genetic modification of a plant with a gene from a non-crossable species or with a synthetic gene.

In one embodiment, the source from which the genetic information is acquired is formed by plants grown from the deposited seeds, or by sexual or vegetative descendants thereof.

Progeny also encompasses plants that carry the trait of the invention which are obtained from other plants of the invention by vegetative propagation or multiplication.

The invention also relates to propagation material suitable for producing a *Lactuca* plant which may comprise the genetic determinant, which when homozygously present in a seed, provides the seed in an unprimed state with the capability to germinate at a high temperature, and wherein said genetic determinant is as present in the seeds of which a representative sample has been deposited under accession number NCIMB 41914, NCIMB 41915, NCIMB 41916, NCIMB 41917, NCIMB 41918, NCIMB 41919, NCIMB 41922, NCIMB 41923, and NCIMB 41926.

In one embodiment, the propagation material is suitable for sexual reproduction. Such propagation material may comprise for example microspores, pollen, ovaries, ovules, embryo sacs and egg cells. In another embodiment, the propagation material is suitable for vegetative reproduction. Such propagation material may comprise for example cuttings, roots, stems, cells, protoplasts, and tissue cultures of regenerable cells, parts of the plant that are suitable for preparing tissue cultures, in particular leaves, pollen, embryos, cotyledons, hypocotyls, meristematic cells, root tips, anthers, flowers, seeds and stems.

The invention further relates to a lettuce plant grown or regenerated from the said propagation material of a plant of the invention, which plant may comprise the genetic determinant, which when homozygously present in a seed, provides the seed in an unprimed state with the capability to germinate at a high temperature.

The invention also relates to a food product which may comprise one or more harvested parts of lettuce plants of the invention, to food products which may comprise harvested leaves of lettuce plants of the invention, either in natural or in processed form, and to a container which may comprise one or more lettuce plants of the invention in a growth substrate for harvest of leaves from the lettuce plant in a domestic environment. The harvested part or food product may be, or comprise the lettuce head and/or leaves of a lettuce plant of the invention. The food product or harvested part, may have undergone one or more processing steps. Such a processing step might comprise but is not limited to any one of the following treatments or combinations thereof: cutting, washing, or a salad mixture which may comprise leaves of the lettuce plant of the invention. The processed form that is obtained is also part of the invention. All the food products and harvested parts carry in their genome the genetic determinant or mutation that when homozygously present leads to the seed having the capability to germinate at a high temperature in an unprimed state.

The invention further relates to a cell of a lettuce plant of the invention, which cell may comprise a genetic determinant, which when homozygously present in a seed, provides the seed in an unprimed state with the capability to germinate at a high temperature, wherein said genetic determinant is as present in or obtainable from a lettuce plant grown from seeds of which a representative sample was deposited under accession number NCIMB 41914, NCIMB 41915, NCIMB 41916, NCIMB 41917, NCIMB 41918, NCIMB 41919, NCIMB 41922, NCIMB 41923, and NCIMB 41926. The said cell thus may comprise the genetic information encoding the trait of the invention, in particular genetic information which is substantially identical, preferably completely identical to the genetic information encoding the said trait of the lettuce plant grown from seeds of which a representative sample was deposited under accession numbers NCIMB 41914, NCIMB 41915, NCIMB 41916, NCIMB 41917, NCIMB 41918, NCIMB 41919, NCIMB 41922, NCIMB 41923, and NCIMB 41926, more in particular the genetic determinant described herein. Preferably, the cell of the invention is part of a plant or plant part, but the cell may also be in isolated form.

The invention also relates to a cell of a lettuce plant of the invention, which cell may comprise a genetic determinant in its genome, which when homozygously present in a seed, provides the seed in an unprimed state with the capability to germinate at a high temperature, and which plant is obtainable by or obtained by transferring the trait of the invention as found in seeds that were deposited under accession numbers NCIMB 41914, NCIMB 41915, NCIMB 41916, NCIMB 41917, NCIMB 41918, NCIMB 41919, NCIMB 41922, NCIMB 41923, and NCIMB 41926 into an agronomically valuable lettuce plant.

The invention further relates to seed of the lettuce plant of the invention, which seed contain in their genome the genetic information that provides the seed in an unprimed state with the capability to germinate at a high temperature.

The invention also relates to the use of seeds of which a representative sample was deposited under accession numbers NCIMB 41914, NCIMB 41915, NCIMB 41916, NCIMB 41917, NCIMB 41918, NCIMB 41919, NCIMB 41922, NCIMB 41923, and NCIMB 41926 for transferring the genetic determinant or mutation, which when homozygously present in a seed, provides the seed in an unprimed state with the capability to germinate at a high temperature, into another agronomically valuable lettuce plant.

The invention also relates to the use of a lettuce plant of the invention that may comprise a genetic determinant or mutation, which when homozygously present in a seed, provides the seed in an unprimed state with the capability to germinate at a high temperature, as found in seeds of which a representative sample was deposited under accession number NCIMB 41914, NCIMB 41915, NCIMB 41916, NCIMB 41917, NCIMB 41918, NCIMB 41919, NCIMB 41922, NCIMB 41923, and NCIMB 41926, as a crop.

The invention also relates to the use of a lettuce plant of the invention that may comprise a genetic determinant or mutation, which when homozygously present in a seed, provides the seed in an unprimed state with the capability to germinate at a high temperature, as found in seeds of which a representative sample was deposited under accession number NCIMB 41914, NCIMB 41915, NCIMB 41916, NCIMB 41917, NCIMB 41918, NCIMB 41919, NCIMB 41922, NCIMB 41923, and NCIMB 41926, as a source of seed.

The invention also relates to the use of a lettuce plant of the invention that may comprise a genetic determinant or mutation, which when homozygously present in a seed, provides the seed in an unprimed state with the capability to germinate at a high temperature, as found in seeds of which a representative sample was deposited under accession number NCIMB 41914, NCIMB 41915, NCIMB 41916, NCIMB 41917, NCIMB 41918, NCIMB 41919, NCIMB 41922, NCIMB 41923, and NCIMB 41926, as a source of propagating material.

The invention also relates to the use of a lettuce plant of the invention that may comprise a genetic determinant or mutation, which when homozygously present in a seed, provides the seed in an unprimed state with the capability to germinate at a high temperature, as found in seeds of which a representative sample was deposited under accession number NCIMB 41914, NCIMB 41915, NCIMB 41916, NCIMB 41917, NCIMB 41918, NCIMB 41919, NCIMB 41922, NCIMB 41923, and NCIMB 41926, for consumption.

In one aspect the invention relates to a method for production of a *Lactuca sativa* L. plant carrying a genetic determinant or mutation, which when homozygously present in a seed, provides the seed in an unprimed state with the capability to germinate at a high temperature, comprising a) crossing a plant which may comprise a genetic determinant or mutation that leads to the trait with another plant;

b) selfing the resulting F1 for obtaining F2 plants;

c) allowing the F2 plants to produce F3 seed and determining the GT50 Dark of the F3 seed lot;

d) selecting plants that have the trait in the F2;

e) optionally performing one or more additional rounds of selfing or crossing, and subsequently selecting, for a plant which may comprise/show the trait of the invention.

It is clear that the parent that provides the trait of the invention is not necessarily a plant grown directly from the deposited seeds. The parent may also be a progeny plant from the seed or a progeny plant from seeds that are identified to have the trait of the invention by other means.

In one aspect, the invention relates to a method for production of a *Lactuca sativa* L. plant carrying a genetic determinant or mutation, which when homozygously present in a seed, provides the seed in an unprimed state with the capability to germinate at a high temperature, comprising a) crossing a plant which may comprise the genetic determinant or mutation that leads to the trait with another plant;

b) optionally backcrossing the resulting F1 with the preferred parent;

c) allowing the F2 plants to produce F3 seed and determining the GT50 Dark of the F3 seed lot;

d) selecting for plants that have the trait in the F2;

e) optionally performing one or more additional rounds of selfing or crossing, and subsequently selecting, for a plant which may comprise the trait.

The invention additionally provides a method of introducing another desired trait into a *Lactuca sativa* L. plant carrying a genetic determinant or mutation, which when homozygously present in a seed, provides the seed in an unprimed state with the capability to germinate at a high temperature, comprising:

a) crossing a *Lactuca sativa* L. plant carrying a genetic determinant or mutation, which when homozygously present in a seed, provides the seed in an unprimed state with the capability to germinate at a high temperature, representative seed of which were deposited under deposit number NCIMB 41914, NCIMB 41915, NCIMB 41916, NCIMB 41917, NCIMB 41918, NCIMB 41919, NCIMB 41922, NCIMB 41923, and NCIMB 41926, with a second *Lactuca sativa* L. plant that may comprise another desired trait to produce F1 progeny;

b) selecting an F1 progeny that may comprise said genetic determinant or mutation, which when homozygously present provides the seed in an unprimed state to germinate at a high temperature and the other desired trait;

c) crossing the selected F1 progeny with either parent, to produce backcross progeny;

d) selecting backcross progeny which may comprise the other desired trait and the genetic determinant or mutation, which when homozygously present provides the seed in an unprimed state to germinate at a high temperature; and e) optionally repeating steps c) and d) one or more times in succession to produce selected fourth or higher backcross progeny that may comprise the other desired trait and the genetic determinant or mutation, which when homozygously present provides the seed in an unprimed state to germinate at a high temperature. The invention includes a *Lactuca sativa* L. plant produced by this method.

In another aspect of the invention selection for the trait of the invention is started in the F2 of a cross or alternatively of a backcross. Selection of plants in the F2 may be done phenotypically as well as by using the a molecular marker(s) which directly or indirectly detect the genetic determinant underlying the trait.

In one embodiment selection for plants having the genetic determinant, which when homozygously present provides the seed in an unprimed state to germinate at a high temperature, is started in the F3 or a later generation.

In one embodiment the plant which may comprise the genetic determinant or mutation is a plant of an inbred line, a hybrid, a doubled haploid, or of a segregating population.

The invention further provides a method for the production of a *Lactuca sativa* L. plant having the genetic determinant or mutation, which when homozygously present provides the seed in an unprimed state with the capability to germinate at a high temperature, by using a doubled haploid generation technique to generate a doubled haploid line which may comprise the said trait.

The invention furthermore relates to hybrid seed that may be grown into a plant having the genetic determinant or mutation, which when homozygously present provides the seed in an unprimed state with the capability to germinate at a high temperature, and to a method for producing such hybrid seed which may comprise crossing a first parent plant with a second parent plant and harvesting the resultant hybrid seed, wherein said first parent plant and/or said second parent plant is a plant as claimed.

In one embodiment, the invention relates to a method for producing a hybrid *Lactuca sativa* L. plant that has the genetic determinant, which when homozygously present provides the seed in an unprimed state with the capability to germinate at a high temperature, which may comprise crossing a first parent *Lactuca sativa* L. plant with a second parent *Lactuca sativa* L. plant and harvesting the resultant hybrid seed, of which the first parent plant and/or the second parent plant has the genetic determinant or mutation, which when homozygously present provides the seed in an unprimed state with the capability to germinate at a high temperature, and growing said hybrid seeds into hybrid plants having the genetic determinant or mutation, which when homozygously present provides the seed in an unprimed state with the capability to germinate at a high temperature.

The invention also relates to a method for the production of a *Lactuca sativa* L. plant having the genetic determinant or mutation, which when homozygously present provides the seed in an unprimed state with the capability to germinate at a high temperature, by using a seed that may comprise the genetic determinant or mutation, which when homozygously present provides the seed in an unprimed state with the capability to germinate at a high temperature, for growing the said *Lactuca sativa* L. plant. The seeds are suitably seeds of which a representative sample was deposited with the NCIMB under deposit number NCIMB 41914, NCIMB 41915, NCIMB 41916, NCIMB 41917, NCIMB 41918, NCIMB 41919, NCIMB 41922, NCIMB 41923, and NCIMB 41926.

The invention also relates to a method for seed production which may comprise growing *Lactuca sativa* L. plants from seeds of which a representative sample was deposited with the NCIMB under deposit number NCIMB 41914, NCIMB 41915, NCIMB 41916, NCIMB 41917, NCIMB 41918, NCIMB 41919, NCIMB 41922, NCIMB 41923, and NCIMB 41926, allowing the plants to produce seeds, and harvesting those seeds. Production of the seeds is suitably done by crossing or selfing. Preferably, the seeds so produced have the capability to germinate at a high temperature.

In one embodiment, the invention relates to a method for the production of a *Lactuca sativa* L. plant having the genetic determinant or mutation, which when homozygously present provides the seed in an unprimed state with the capability to germinate at a high temperature, by using tissue culture.

The invention furthermore relates to a method for the production of a *Lactuca sativa* L. plant having the genetic determinant or mutation, which when homozygously present provides the seed in an unprimed state with the capability to germinate at a high temperature, by using vegetative reproduction.

In one embodiment, the invention relates to a method for the production of a *Lactuca sativa* L. plant having the genetic determinant or mutation, which when homozygously present provides the seed in an unprimed state with the capability to germinate at a high temperature, by using a method for genetic modification to introgress the said trait into the *Lactuca sativa* L. plant. Genetic modification may comprise transgenic modification or transgenesis, using a gene from a non-crossable species or a synthetic gene, and cisgenic modification or cisgenesis, using a natural gene, coding for an (agricultural) trait, from the crop plant itself or from a sexually compatible donor plant.

The invention also relates to a breeding method for the development of *Lactuca sativa* L. plants having the genetic determinant or mutation, which when homozygously present provides the seed in an unprimed state with the capability to germinate at a high temperature wherein germplasm which may comprise said genetic determinant, mutation or trait is used. Representative seed of said plant which may comprise the genetic determinant or mutation and being representative for the germplasm was deposited with the NCIMB under deposit number NCIMB 41914, NCIMB 41915, NCIMB 41916, NCIMB 41917, NCIMB 41918, NCIMB 41919, NCIMB 41922, NCIMB 41923, and NCIMB 41926.

In a further embodiment the invention relates to a method for the production of a *Lactuca sativa* L. plant having the genetic determinant or mutation, which when homozygously present provides the seed in an unprimed state with the capability to germinate at a high temperature, wherein progeny or propagation material of a plant which may comprise the genetic determinant or mutation conferring said trait is used as a source to introgress the said trait into another *Lactuca sativa* L. plant. Representative seed of said plant which may comprise the genetic determinant was deposited with the NCIMB under deposit number NCIMB 41914, NCIMB 41915, NCIMB 41916, NCIMB 41917, NCIMB 41918, NCIMB 41919, NCIMB 41922, NCIMB 41923, and NCIMB 41926.

The invention provides preferably a *Lactuca sativa* L. plant having the genetic determinant or mutation, which when homozygously present provides the seed in an unprimed state with the capability to germinate at a high temperature, which plant is obtainable by any of the methods herein described and/or familiar to the skilled person.

In another embodiment, the invention relates to a method for obtaining a lettuce plant of the species *Lactuca sativa* L. carrying a mutation, which when homozygously present in a seed, provides the seed in an unprimed state with the capability to germinate at a high temperature, comprising:

a) treating M0 seeds of a lettuce plant to be modified with a mutagenic agent to obtain M1 seeds;
b) growing plants from the thus obtained M1 seeds to obtain M1 plants;
c) producing M2 seeds by self-fertilization of M1 plants; and
d) optionally repeating step b) and c) n times to obtain M1+n seeds.

The M1+n seeds thus obtained are germinated at a high temperature. Subsequently, any seeds that germinate are grown into plants. For confirmation, these plants are then self-fertilized to produce additional progeny seed, which are preferably germinated at a high germination temperature and under continuous dark conditions (24 h/day). The confirmed seeds are grown into plants, and these are optionally multiplied one or more further generations while continuing to select for the ability to germinate at a high temperature.

An example of a well-known mutagen is Ethyl Methane Sulfonate (EMS). EMS alkylates primarily G residues of a DNA strand which during DNA replication causes pairing with the T instead of C. Therefore, GC base pairs change to AT base pairs at a frequency which is determined by the effective dose of EMS and the activity of the mismatch repair system of the plant. The effective dose of EMS depends on the concentration used, the seed size and other physical properties and the time of incubation of the seeds in the EMS solution. The seeds which have been treated with EMS are typically called M1 seeds. As a consequence of the treatment, the tissues of the M1 seeds contain random point mutations in the genomes of their cells and those present in the subpopulation of cells which will form the germline tissue (germinal cells) will be transferred to the next generation which is called the M2. It should be noted that although most EMS induced mutations and the resulting trait are monogenic recessive, there is a possibility that monogenic dominant mutations leading to a monogenic dominant traits may occur. Furthermore, mutations or combinations thereof which are haplo-insufficient thereby causing sterility or which induce embryo lethality will not be transferred to the M2 generation.

A similar procedure as described above for the use of EMS applies for other mutagenic agents as well. Other mutagenic agents include but are not limited to, diethyl sufate (des), ethyleneimine (ei), propane sultone, N-methyl-N-nitrosourethane (mnu), N-nitroso-N-methylurea (NMU), N-ethyl-N-nitrosourea(enu), and sodium azide.

Alternatively, the mutations are induced by means of irradiation, which is for example selected from x-rays, fast neutrons, UV radiation.

In another embodiment of the invention, the mutations are induced by means of genetic engineering, such as by means of using chimeric oligonucleotides, homologous recombination, introduction of modified target genes which complete with the endogenous product, downregulation through RNA interference, etc.

The technology which allows modification of gene targets in the genome of a plant in a specific manner is known to the person skilled in the art. For example, chimeric oligonucleotides have been demonstrated to be effective mutagens with a specific mode of action. Another approach is to modify gene targets through homologous recombination or gene targeting. Using such an approach, a fragment of a gene is exchanged by an introduced DNA fragment containing a desired modification. Transgenic approaches are also feasible in which modified target genes are introduced which compete with the endogenous product. This may lead to dominant negative effects. Moreover specific downregulation of the expression of genes is feasible through RNA interference.

In this application the words "genetic determinant" and "mutation" are sometimes used together and sometimes not. It is to be understood that the genetic determinant may be a mutation and that the mutation may also be indicated as a genetic determinant. The two terms may thus be used interchangeably.

Although the present invention and its advantages have been described in detail, it should be understood that various changes, substitutions and alterations may be made herein without departing from the spirit and scope of the invention as defined in the appended claims.

The present invention will be further elucidated in the examples that follow. These examples are for illustration purposes only and are not to be construed as limiting this invention in any way.

EXAMPLES

Example 1

Genetic Modification of Lettuce Seeds by Ethyl Methane Sulfonate (EMS)

Seeds of the wild type lettuce varieties Apache, Sensaï Troubadour, and Yorvik (all four from Rijk Zwaan, De Lier, The Netherlands) were treated with EMS by submergence of approximately 2000 seeds per variety into an aerated solution of either 0.5% (w/v) or 0.7% EMS for 24 hours at room temperature.

Approximately 1500 treated seeds per variety per EMS dose were germinated and the resulting plants were grown in a greenhouse in The Netherlands from May to September to produce seeds.

Following maturation, M2 seeds were harvested and bulked in one pool per variety per treatment. The resulting eight pools of M2 seeds were used as starting material to identify the individual M2 seeds containing high temperature germination alleles.

The efficacy of the genetic modification procedure was assessed by determining the occurrence of bleached plants, which is indicative for chlorophyll loss due to modification in genes directly or indirectly involved in the formation or accumulation of chlorophyll. Individual plants from all 8 pools of M2 seeds were observed to be bleached. This demonstrates that the applied treatments resulted in genetic modifications.

Example 2

Identification of Lettuce Seeds Capable of Germinating at a High Temperature

Lettuce seeds capable of germinating at a high temperature were identified amongst the M2 seeds that were produced as a result of the EMS treatment described in Example 1.

Of each of the 8 available M2 pools, approximately 2000 seeds were germinated on wetted filter paper in a closed container. The M2 seeds of Apache, Yorvik and Troubadour were incubated at 34° C., whilst the M2 seeds of Sensaï were incubated at 32° C., under continuous dark conditions (24 h/day) in order to mimic natural germination conditions beneath the soil or when seeds are encapsulated in pellets.

Any seeds that germinated at the given temperatures were grown into plants. These plants were self-fertilized to produce M3 seed. The M3 seeds were again germinated at 34° C. under continuous dark conditions, to confirm the presence of high temperature germination alleles.

The confirmed M3 seeds were grown into M3-lines which were then multiplied, representative seeds of which were deposited with the NCIMB under accession numbers NCIMB 41914, NCIMB 41915, NCIMB 41916, NCIMB 41917, NCIMB 41918, NCIMB 41919, NCIMB 41922, NCIMB 41923, and NCIMB 41926.

Example 3A

Seed Germination Testing

Germination tests were performed at different temperatures, to determine the cumulative germination over time at a given temperature for each seed lot of wild type lettuce varieties Apache, Sensaï, Troubadour, and Yorvik, as well as the EMS treated seeds of the deposit (obtained in Example 2).

For each seed lot, 100 seeds were sown on top of round filter paper, which was wetted with tap water. The seeds sown on the round filter paper were in turn placed inside a non-transparent plastic tray, which itself was lined with a large square piece of beet filter paper wetted with tap water. Additionally, a temperature recording device was placed on the beet filter paper to record the actual germination temperature at seed level. The tray was then closed with a well-fitted non-transparent lid, and wrapped inside a layer of dark plastic. The trays were placed inside a pre-heated incubator at the desired temperature. The germination tests were conducted from 18° C. to 42° C. Biological replicates were sown in different trays and preferably at different points in time to remove any biases related to sowing.

All precautions were taken to ensure that the germination tests were performed under dark conditions. Setting up the germination tests, the incubations and the germination scoring were all performed inside a thermostable room, closed from all outside light sources. In order to prevent any light effects on the germination, the room was lit with green safe lights (Philips TL-D 36W/17 Green).

Germination was scored twice a day. A seed was scored as being germinated when a visible radical protrusion through the pericarp of the seed could be observed. "Germination over Time" curves were plotted to show the cumulative germination of a given seed lot over time, at the set temperature. Amongst other parameters, the final germination percentage for a given seed lot at a given temperature, could also be determined from the "Germination over Time" curve.

Example 3B

Determining the GT50 Dark of a Seed Lot

To determine the GT50 Dark of a given seed lot, the final germination percentage from each "Germination over Time" curve from Example 3A, was plotted per actual measured temperature, from 18° C. to 42° C. (FIGS. 1A, 1B, and 1C). A line of best fit was used to fit the final germination percentages into a curve.

The GT50 Dark was derived per seed lot, by determining the temperature at which the final germination percentage is expected to be 50% (Table 1). When seeds of a given seed lot are exposed to temperatures above the GT50 Dark, they may become thermodormant or die.

It is clear from FIGS. 1A, 1B, and 1C and Table 1 (Relative increase in GT50 Dark between mutant seed lots and wild type seed lots) that the GT50 Dark of the seed lots which may comprise unprimed seeds of the invention which carry a mutation in the homozygous state, is significantly higher than seed lots which may comprise unprimed seeds which do not carry the said mutation. This illustrates that the capability of a seed of the invention to germinate at a high temperature results directly from the said mutation.

TABLE 1

GT50 Dark of mutant seed lots and wild type seed lots.

| Seed name or number | Origin | GT50 Dark (° C.) | Relative increase in GT50 Dark between mutant seed lots and wild type seed lots (° C.) |
|---|---|---|---|
| Apache | — | 28.7 | — |
| Sensaï | — | 28.1 | — |
| Troubadour | — | 29.0 | — |
| Yorvik | — | 20.0 | — |
| NCIMB 41919 | Y | 35.6 | 15.6 |
| NCIMB 41922 | Y | 33.3 | 13.3 |
| NCIMB 41923 | S | 39.2 | 11.1 |
| NCIMB 41914 | T | 36.2 | 7.2 |
| NCIMB 41915 | T | 38.0 | 9.0 |
| NCIMB 41916 | T | 38.3 | 9.3 |
| NCIMB 41917 | T | 39.3 | 10.3 |
| NCIMB 41926 | A | 40.1 | 11.4 |
| NCIMB 41918 | A | 36.6 | 7.9 |

A = Apache; S = Sensaï; T = Troubadour; Y = Yorvik.

Example 4

Transferring of the Trait of the Invention to Other Lettuce Plants

A lettuce plant of the invention was crossed with a wild type (WT) lettuce plant of the incised leaf type, which does not carry the trait of the invention.

The GT50 Dark of the resulting F1 seeds was determined as described in Examples 3A and 3B. F1 seeds had the same GT50 Dark as the seeds of the WT plants (e.g. the seeds were not capable of germinating at a high temperature).

From the F1 population which was grown from the F1 seeds, a plant was selected which was selfed to obtain a population of F2 plants. The F2 plants were again selfed to produce F3 seeds and the GT50 Dark of the corresponding F3 seed lot was determined. If the GT50 Dark of a given F3 seed lot was at least 31.8° C., the corresponding F2 plant from which it was derived, contained the genetic determinant. If the GT50 Dark of a given seed lot was lower than 31.8° C., the corresponding F2 plant from which it was derived either did not contain the genetic determinant, or contained the genetic determinant in a heterozygous manner. Based on the GT50 Dark of the F3 seed lots, the F2 segregated in a manner that corresponded to a monogenic recessive inheritance of the trait of the invention.

The invention is further described by the following numbered paragraphs:

1. A seed lot of the species *Lactuca sativa* L. wherein the seeds belonging to the seed lot comprise a genetic determinant, which when homozygously present, provides the seeds in an unprimed state with the capability to germinate at a high temperature, and which seed lot is characterized in that the GT50 Dark of said seed lot is at least 6.2° C. higher than the GT50 Dark of a seed lot of seeds not comprising the genetic determinant, and wherein said genetic determinant is as present in seeds of which a representative sample has been deposited under accession number NCIMB 41914, NCIMB 41915, NCIMB 41916, NCIMB 41917, NCIMB 41918, NCIMB 41919, NCIMB 41922, NCIMB 41923, and NCIMB 41926.
2. The seed lot as described in paragraph 1, wherein the GT50 Dark of said seed lot is in order of increased preference between 6.5° C. and 22° C., between 7° C. and 22° C., between 8° C. and 22° C., between 9° C. and 22° C., between 10° C. and 22° C., between 11° C. and 22° C., between 12° C. and 22° C., between 13° C. and 22° C., between 14° C. and 22° C., between 15° C. and 22° C., between 16° C. and 22° C. between 17° C. and 22° C. between 18° C. and 22° C. between 19° C. and 22° C. between 20° C. and 22° C. and between 21° C. and 22° C. higher.
3. The seed lot as described in paragraph 1 or 2, wherein the GT50 Dark of the seed lot is at least 31.8° C.
4. The seed lot as described in any one of the paragraphs 1-3, wherein the GT50 Dark of the seed lot in order of increased preference lies between 31.8° C. and 42° C., between 32° C. and 42° C., between 33° C. and 42° C., between 34° C. and 42° C., between 35° C. and 42° C., between 36° C. and 42° C., between 37° C. and 42° C., between 38° C. and 42° C., between 39° C. and 42° C., between 40° C. and 42° C., between 41° C. and 42° C.
5. A lettuce plant of the species *Lactuca sativa* L. carrying a genetic determinant, which when homozygously present in a seed, provides the seed in an unprimed state with the capability to germinate at a high temperature, as defined in any one of the paragraphs 1-4.
6. A seed belonging to a seed lot as described in any one of the paragraphs 1-4.
7. A lettuce plant of paragraph 6, grown from seed of which a representative sample has been deposited under accession number NCIMB 41914, NCIMB 41915, NCIMB 41916, NCIMB 41917, NCIMB 41918, NCIMB 41919, NCIMB 41922, NCIMB 41923, and NCIMB 41926.
8. Progeny of a lettuce plant as described in paragraphs 6 or 7, carrying a genetic determinant, which when homozygously present in a seed, provides the seed in an unprimed state with the capability to germinate at a high temperature, as defined in any one of the paragraphs 1-4.
9. Propagation material derived from a plant as described in paragraphs 6 or 7, carrying a genetic determinant, which when homozygously present in a seed, provides the seed in an unprimed state with the capability to germinate at a high temperature, as defined in any one of the paragraphs 1-4.
10. Propagation material capable of growing into a plant as described in paragraphs 6 or 7, carrying a genetic determinant, which when homozygously present in a seed, provides the seed in an unprimed state with the capability to germinate at a high temperature, as defined in any one of the paragraphs 1-4.
11. Propagation material as described in paragraph 9 or 10, wherein the propagation material is selected from the group consisting of microspores, pollen, ovaries, ovules, embryos, embryo sacs, egg cells, cuttings, roots, root tips, hypocotyls, cotyledons, stems, leaves, flowers, anthers, seeds, meristematic cells, protoplasts, and cells.
12. Tissue culture of propagation material as described in any one of the paragraphs 9 to 11.
13. Harvested part of a lettuce plant as described in paragraphs 6 or 7, which harvested part is in particular a lettuce head and/or leaf, and is optionally in processed form.
14. Harvested part of a lettuce plant as described in paragraph 13, wherein the harvested part is a food product.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A seed lot of the species *Lactuca sativa L.* wherein the seeds belonging to the seed lot comprise a genetic determinant, which when homozygous present, provides the seeds in an unprimed state with the capability to germinate at a high temperature, and which seed lot is characterized in that the GT50 Dark of said seed lot is at least 6.2° C. higher than the GT50 Dark of a seed lot of wild type seeds not comprising the genetic determinant, and wherein said genetic determinant is as present in seeds of which a representative sample has been deposited under accession number NCIMB 41914, NCIMB 41915, NCIMB 41916, NCIMB 41917, NCIMB 41918, NCIMB 41919, NCIMB 41922, NCIMB 41923, or NCIMB 41926.

2. The seed lot as claimed in claim 1, wherein the difference in the GT50 Dark of said seed lot compared to wild type is in order of increased preference between 6.5° C. and 22° C., between 7° C. and 22° C., between 8° C. and 22° C., between 9° C. and 22° C., between 10° C. and 22° C., between 11° C. and 22° C., between 12° C. and 22° C., between 13° C. and 22° C., between 14° C., and 22° C., between 15° C. and 22° C., between 16°C. and 22° C. between 17° C. and 22° C. between 18° C. and 22° C. between 19° C. and 22° C. between 20° C. and 22° C., or between 21° C. and 22° C. higher.

3. The seed lot as claimed in claim 1, wherein the GT50 Dark of the seed lot is at least 31.8° C.

4. The seed lot as claimed in claim 1, wherein the GT50 Dark of the seed lot in order of increased preference lies between 31.8° C. and 42° C., between 32° C. and 42° C., between 33° C. and 42° C., between 34° C. and 42° C., between 35° C. and 42° C., between 36° C. and 42° C., between 37° C. and 42° C., between 38° C. and 42° C., between 39° C. and 42° C., between 40° C. or 42° C.

5. A seed belonging to a seed lot as claimed in claim 1.

6. A lettuce plant of the species *Lactuca sativa L.* carrying the genetic determinant of claim 1., which when homozygous present in a seed of the plant, provides the seed in an unprimed state with the capability to germinate at a high temperature.

7. The lettuce plant of claim 6, grown from seed of which a representative sample has been deposited under accession number NCIMB 41914, NCIMB 41915, NCIMB 41916, NCIMB 41917, NCIMB 41918, NCIMB 41919, NCIMB 41922, NCIMB 41923, or NCIMB 41926.

8. Progeny of a lettuce plant as claimed in claim 6, carrying the genetic determinant, which when homozygous present in a seed, provides the seed in an unprimed state with the capability to germinate at a high temperature.

9. Propagation material derived from a plant as claimed in claim 6, carrying the genetic determinant, which when ihomozygously present in a seed, provides the seed in an unpritned state with the capability to germinate at a high temperature.

10. Propagation material as claimed in claim 9, wherein the propagation material is selected from the group consisting of microspores, pollen, ovaries, ovules, embryos, embryo sacs, egg cells, cuttings, roots, root tips, hypocotyls, cotyledons, stems, leaves, flowers, anthers, seeds, meristematic cells, protoplasts, and cells.

11. A tissue culture of propagation material as claimed in claim 9.

12. Propagation material capable of growing into a plant as claimed in claim 6, carrying the genetic determinant, which when homozygous present in a seed, provides the seed in an unprimed state with the capability to germinate at a high temperature.

13. Propagation material as claimed in claim 12, wherein the propagation material is selected from the group consisting of microspores, pollen, ovaries, ovules, embryos, embryo sacs, egg cells, cuttings, roots, root tips, hypocotyls, cotyledons, stems, leaves, flowers, anthers, seeds, meristematic cells, protoplasts, and cells.

14. A tissue culture of propagation material as claimed in claim 12.

15. A harvested part of a lettuce plant as claimed in claim 6, which harvested part is in particular a lettuce head and/or leaf, and is optionally in processed form.

16. The harvested part of a lettuce plant as claimed in claim 15, wherein the harvested part is a food product.

* * * * *